(12) United States Patent
Kozma et al.

(10) Patent No.: US 8,195,580 B2
(45) Date of Patent: Jun. 5, 2012

(54) METHODS OF DETECTION OF PROPOGATING PHASE GRADIENTS USING MODEL FIELD THEORY OF NON-GAUSSIAN MIXTURES

(75) Inventors: Robert Kozma, Memphis, TN (US); Leonid Perlovsky, Brookline, MA (US)

(73) Assignees: The University of Memphis Research Foundation, Memphis, TN (US); The United States of America, as Represented by the Secretary of the Air Force, Washington, DC (US)

( * ) Notice: Subject to any disclaimer, the term of this patent is extended or adjusted under 35 U.S.C. 154(b) by 1014 days.

(21) Appl. No.: 12/156,237

(22) Filed: May 30, 2008

(65) Prior Publication Data

US 2009/0299704 A1 Dec. 3, 2009

(51) Int. Cl.
*G06F 19/24* (2011.01)
*G06F 17/10* (2006.01)
*G06K 9/62* (2006.01)

(52) U.S. Cl. .............................. 706/1; 706/20
(58) Field of Classification Search .................. 706/1
See application file for complete search history.

(56) References Cited

U.S. PATENT DOCUMENTS

2004/0073414 A1 4/2004 Bienenstock et al.
2007/0046486 A1 3/2007 Donoghue et al.

OTHER PUBLICATIONS

Robert Kozma et al., Estimation of Propagating Phase Transients in EEG Data Application of Dynamic Logic Neural Modeling Approach. Proceedings of International Joint Conference on Neural Networks [online], Aug. 12-17, 2007 [retrieved on Aug. 31, 2011]. Retrieved from the Internet< URL:http://ieeexplore.ieee.org/stamp/stamp.jsp?arnumber=04371324>.*
Freeman, "A neurobiological theory of meaning in perception. Part 2. Spatial patterns of phase in gamma EEG from primary sensory cortices reveal the properties of mesoscopic wave packets" International Journal of Bifurcation and Chaose. (2003).
Korsmo, "An Experiment to Search Exotic Resonances in Proton-Anitproton Collisions at CERN's LEAR", Thesis, University of Oslo 1990.
International Search Report, International Application No. PCT/US09/46032 (Aug. 5, 2009).
Written Opinion of the International Searching Authority, International Application No. PCT/US09/46032 (Aug. 5, 2009).
International Preliminary Report on Patentability, International Application No. PCT/US09/46032 (Nov. 30, 2010).

* cited by examiner

*Primary Examiner* — Jeffrey A Gaffin
*Assistant Examiner* — Nathan Brown, Jr.
(74) *Attorney, Agent, or Firm* — Edwards Wildman Palmer LLP; Peter F. Corless; Brian R. Landry

(57) ABSTRACT

Methods, computer-readable media, and systems are provided for the detection of propagating phase gradients using model field theory of non-Gaussian mixtures. One embodiment of the invention is directed to a method for identifying phase cones in a data set. The method includes generating an initial set of values of parameters ($\xi_A, \eta_A, t_A$) for a preset number of cones, initializing a covariance matrix with high values, evaluating the ratio of volume of a phase cone over total observed space-time volume, comparing the data set with a model, estimating a class probability density function, and generating a revised set of values of parameters ($\xi_A, \eta_A, t_A$).

14 Claims, 3 Drawing Sheets

METHODS OF DETECTION OF PROPOGATING PHASE GRADIENTS USING MODEL FIELD THEORY OF NON-GAUSSIAN MIXTURES

STATEMENT AS TO RIGHTS TO INVENTIONS MADE UNDER FEDERAL SPONSORED RESEARCH AND DEVELOPMENT

This invention was made with government support under Grant (Contract) No. USAF F33601-03-F-0203-SC-0023 awarded by the United States Air Force. The U.S. Government has certain rights in this invention.

BACKGROUND

Experimental studies indicate that intermittent synchronization across large cortical areas provides the window for the emergence of meaningful cognitive activity in animals and humans [1, 2]. In neural tissues, populations of neurons send electric currents to each other and produce activation potentials observed in electroencephalography (EEG) experiments. The synchrony among neural units can be evaluated by comparing their activation levels as the function of time. While single unit activations have large variability and do not seem synchronous, the activations of neural groups often exhibit apparent synchrony.

Experimental studies on brain waves at the level of neural populations using EEG techniques gave rise to new theories. Multiple electrode recordings in the olfactory bulb indicated that odors are encoded as complex spatial and temporal patterns in the bulb. Based on these observations, a chaos theory of sensory perception has been proposed [3, 4]. In this approach, the state variables of the brain in general, and the olfactory bulb in particular, traverse along complex chaotic trajectories which constitute a strange attractor with multiple wings. External stimuli constrain the trajectories to one of the attractor wings, which are identified as stimulus specific patterns. Once the stimulus disappears, the dynamics returns to the unconstrained state until the next stimulus arrives.

EEG measurements confirm the presence of the self-sustained, randomized, steady state background activity of brains. This background activity is the source from which ordered states of macroscopic neural activity emerge, like the patterns of waves at the surfaces of deep bodies of water. Neural tissues, however, are not passive media, through which effects propagate like waves in water [5]. The brain medium has an intimate relationship with the dynamics through a generally weak, subthreshold interaction of neurons. The brain activity exhibits high level of synchrony across large cortical regions. The synchrony is interrupted by episodes of desynchronization, when propagation of phase gradients in the activation of local populations can be identified. The spatially ordered phase relationship between cortical signals is called phase cone. Experiments show that phase gradients propagate at velocities up to 2 m/s and can cover cortical areas of several $cm^2$ [1, 6].

SUMMARY OF THE INVENTION

Methods, computer-readable media, and systems are provided for the detection of propagating phase gradients using model field theory of non-Gaussian mixtures. One embodiment of the invention is directed to a method for identifying phase cones in a data set. The method includes (a) generating an initial set of values of parameters $(\xi_A, \eta_A, t_A)$ for a preset number of cones, (b) initializing a covariance matrix with high values, (c) evaluating the ratio of volume of a phase cone over total observed space-time volume, (d) comparing the data set with a model, (e) estimating a class probability density function, (f) evaluating association probabilities, and (g) generating a revised set of values of parameters $(\xi_A, \eta_A, t_A)$.

In some embodiments, the method includes repeating steps (c) through (g) with the revised set of values. Other embodiments include reducing the values of the covariance matrix. The repeating step can be terminated when the revised set of values of parameters $(\xi_A, \eta_A, t_A)$ converge. The ratio of the volume of the phase cone over the total observed space-time volume can be expressed by Equation (18). In other embodiments, $\xi_A$ in the revised set of values of parameters $(\xi_A, \eta_A, t_A)$ is defined by Equation (21). In still other embodiments, $\eta_A$ in the revised set of values of parameters $(\xi_A, \eta_A, t_A)$ is defined by Equation (22). The parameter $t_A$ in the revised set of values of parameters $(\xi_A, \eta_A, t_A)$ can be defined by the Equation (25). The model can be represented by Equation (17). The class probability density function can be represented by the Equation (12). The association probabilities can be represented by Equation (8).

Another embodiment of the invention is directed to a computer-readable medium whose contents cause a computer to perform a method for identifying phase cones in a data set. The method includes (a) generating an initial set of values of parameters $(\xi_A, \eta_A, t_A)$ for a preset number of cones, (b) initializing a covariance matrix with high values, (c) evaluating the ratio of volume of a phase cone over total observed space-time volume, (d) comparing the data set with a model, (e) estimating a class probability density function, (f) evaluating association probabilities, and (g) generating a revised set of values of parameters $(\xi_A, \eta_A, t_A)$.

Yet another embodiment is directed to a system including the computer-readable medium described above and a computer in data communication with the computer-readable medium.

FIGURES

For a fuller understanding of the nature and desired objects of the present invention, reference is made to the following detailed description taken in conjunction with the accompanying drawing figures wherein like reference characters denote corresponding parts throughout the several views and wherein.

DEFINITIONS

Figure 1:
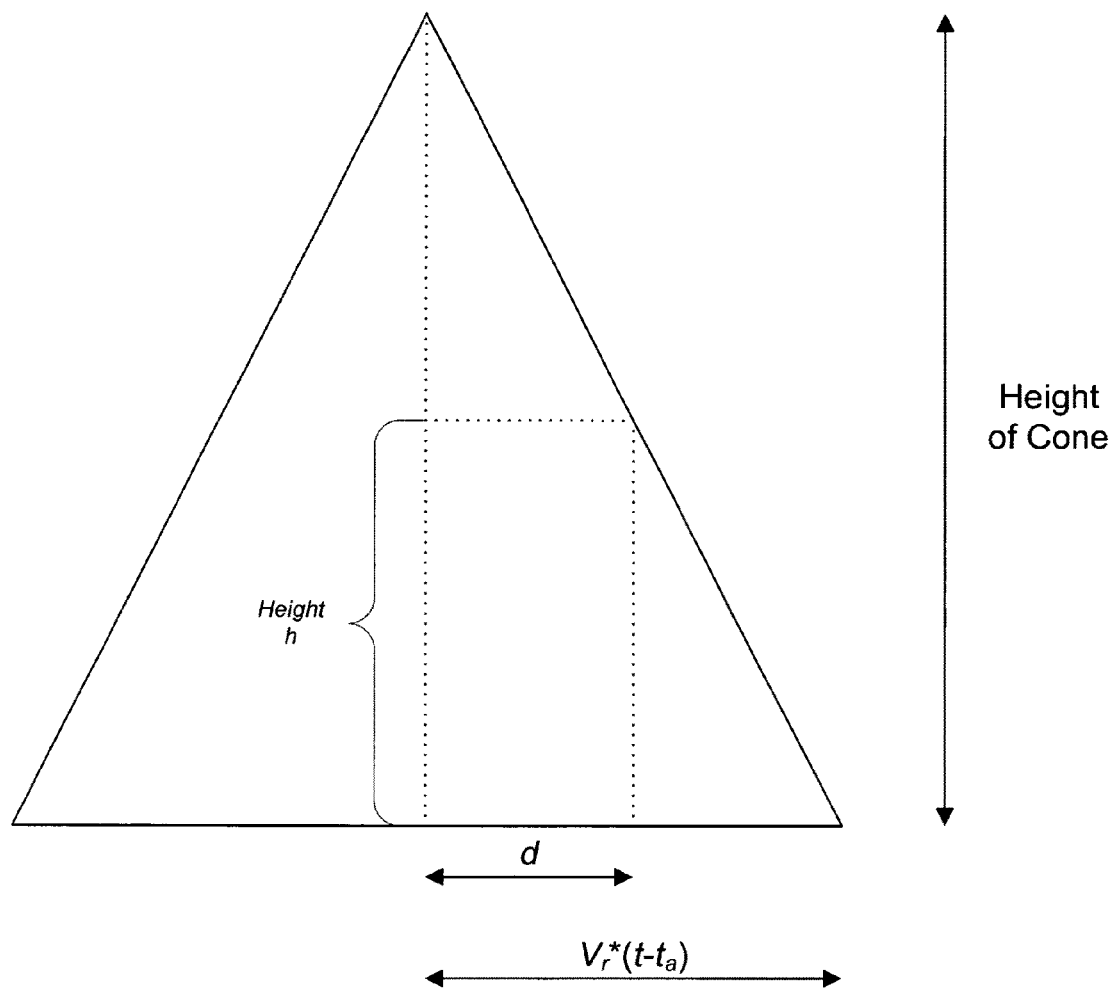
FIG. 1 is a diagram of the cross section of a cone across the apex.

A computer readable medium shall be understood to mean any article of manufacture that contains data that can be read by a computer or a carrier wave signal carrying data that can be read by a computer. Such computer readable media includes, but is not limited to, magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

DESCRIPTION OF THE INVENTION

Embodiments of this invention provide a Dynamic Logic-based method for the identification of spatially distributed phase distributions in EEG data. The inventions herein extend previous studies for time-dependent non-Gaussian phase component patterns. This disclosure derives the corresponding equations of Dynamic Logic, provides an algorithm for the iterative solution of these equations, and demonstrates the proposed methodology using simulated EEG data.

Model Field Theory (MFT) is a well-established methodology of pattern recognition and Dynamic Logic (DL) lies at the heart of MFT [7]. Dynamic logic associates signals with models according to similarities among them. In the process of association-recognition, models are adapted to fit the data and similarity measures are adapted so that their fuzziness is matched to the model uncertainty. The initial uncertainty of the knowledge is high and so is the fuzziness of the similarity measure. Depending on the target problem and the selected adaptation rule, various models can be specified. During learning, the models become more accurate and the similarity more crisp, the value of the similarity measure increases. It is proposed that brains perform fast and robust recognition by adapting the accuracy of their approximation based on the available information on the problem, as it is described by dynamic logic [8]. DL has been applied successfully in a wide range of applications, including automated target recognition, radar imaging, biomedical diagnostics [9-14].

Mathematical Framework of Dynamic Logic
Notations and Maximum Likelihood Equations The statistical method for maximum likelihood estimation presented here is based on the Dynamic Logic (DL) formulation; for details, see [7]. Consider a model consisting of K mixture components. Each component is characterized by its own probability density function $p(X_n|\Theta_k)$. Here $\theta_k$ is the parameter set of the $k^{th}$ component of the mixture model. Let $\theta$ denote the set of all parameters of the mixtures, i.e., $$\Theta = [\Theta_1, \Theta_2, \ldots, \Theta_K] \quad (1)$$

The set of available data is given by $X_n$. Here n is the data index in the space and time. Consider a system having N spatial points, and for each point of space measure T time instances, $n=1, \ldots, N*T$.

The goodness of the fit between the model and the data is often described by the likelihood (L) function [17]:

$$L(\Theta) = \prod_{N,T} p(X_n | \Theta) \quad (2)$$

One searches a parameter set $\theta$ that maximizes L. It is generally easier to work with Log Likelihood (LL) rather than with the likelihood itself. Since the logarithm is monotonically increasing, the value $\theta$ that maximizes LL also maximizes L.

$$LL(\Theta) = \sum_N \sum_T \ln \sum_K r_k(t) p(X_n | \Theta_k) \quad (3)$$

$\theta_k$ is the parameter set of component k, and $r_k(t)$ denotes the relative weight (strength) of component k: $0 \leq r_k(t) \leq 1$. Time-dependent components are considered, therefore $r_k(t)$ is a function of t: $0 \leq t \leq T$. For example, if at time instant $t=t_1$, the value of $r_k(t_1)=0$, it means that component k is not present at the give time instant. According to the DL formulation, the probability density function (pdf) of the k-th component is known $p(X_n|\Theta_k)$ and it depends on space and time coordinates, as well as on the k-th parameters $\theta_k$. Assume that the total weight of all components over all monitored time segment is constant. This leads to the following normalization condition:

$$\sum_T \sum_K r_k(t) = 1 \quad (4)$$

The parameters of mixtures are estimated by maximizing the log-likelihood in Equation (3). Next conditions for the parameters are derived by calculating the partial derivatives of LL with respect to the parameters. The standard method of Lagrangian multipliers is used. By introducing unknown coefficient $\lambda$, the expression for F to be minimized can be written as:

$$\min F = -LL + \lambda \left(1 - \sum_T \sum_K r_k(t)\right) \quad (5)$$

First, derive a general expression for any dynamic functional form of $r_k(t)$. Next, use the specific form corresponding to the given identification problem. After taking the derivative of F with respect to the i-th parameter of the k-th component $\theta_{k,i}$:

$$0 = \frac{\partial F}{\lambda \Theta_{k,i}} = -\frac{\partial LL}{\partial \Theta_{k,i}} - \lambda \sum_T \frac{\partial r_k(t)}{\partial \Theta_{k,i}} \quad (6)$$

In the above Equation (6), the summation over all components K is omitted, as the partial derivative produces nonzero contribution only for component k. Substituting the expression for LL from Equation (4), it is readily obtained:

$$\frac{\partial F}{\partial \Theta_{k,i}} = \quad (7)$$

$$-\sum_T \sum_N P(k|n) \left\{ \frac{\partial \ln(r_k(t))}{\partial \Theta_{k,i}} + \frac{\partial \ln(p(X_n | \Theta_k))}{\partial \Theta_{k,i}} \right\} - \lambda \sum_T \frac{\partial r_k(t)}{\partial \Theta_{k,i}} = 0$$

The association probability $P(k|n)$ as the probability that a given sample n belongs to class k:

$$P(k|n) = \frac{r_k(t) p(X_n | \Theta_k)}{\sum_K r_k(t) p(X_n | \Theta_k)} \quad (8)$$

After some algebra, the following expression for unknown Lagrange parameter $\lambda$ is obtained:

$$\lambda = -\sum_{N,T} P(k\mid n)\frac{\frac{\partial \ln(r_k(t))}{\partial \Theta_{k,i}} + \frac{\partial \ln(p(X_n\mid \Theta_k))}{\partial \Theta_{k,i}}}{\sum_K \partial r_k(t)/\partial \Theta_{k,i}} \quad (9)$$

Multiply both sides of this equation by $r_k(t)$, and sum over all K and T. The left hand side can be simplified by using the normalization condition in Equation (4), and the following expression is obtained for $\lambda$:

$$\lambda = -\sum_{K,T} r_k(t)\sum_{N,T} P(k\mid n)\frac{\frac{\partial \ln(r_k(t))}{\partial \Theta_{k,i}} + \frac{\partial \ln(p(X_n\mid \Theta_k))}{\partial \Theta_{k,i}}}{\sum_K \partial r_k(t)/\partial \Theta_{k,i}} \quad (10)$$

The value of $\lambda$ can be evaluated based on Equation (10) for given values of mixture parameters $\theta_k$, and for known component distributions. In the special case of time invariant constant values of $r_k$, and by performing the partial derivation with respect to weights $r_k$, the value $\lambda = -N$ is found, which is indeed the correct result for the time-independent case [10].

Derivation of Mixture Parameter Equations

Start with Equation (7), where $\lambda$, has a known value, as given by Equation (10). Consider two cases. First, analyze the case when parameter $\theta_{k,i}$ does not explicitly appear in $r_k(t)$. Next those parameters are investigated, which explicitly enter the functional form of $r_k(t)$. It will be shown in the next section that the EEG modeling problem both cases arise.

The Case when $r_k(t)$ does not depending on $\theta_{k,i}$

In this case the second term with coefficient $\lambda$, vanishes and Equation (7) reduces to:

$$-\sum\sum P(k\mid n)\frac{\partial}{\partial \Theta_{k,i}}\{\ln(p(X_n\mid \Theta_k))\} = 0 \quad (11)$$

The probability distribution function $p(X_n\mid \Theta_k)$ for component k is assumed of the following form:

$$p(X_n\mid \Theta_k) = \frac{1}{\sqrt{(2\pi)^3|C_k|}} e^{\{-\frac{1}{2}|X_n-M_n^k|^T C_k^{-1}|X_n-M_n^k|\}} \quad (12)$$

Here $X_n$ denotes the experimental (measured) data points in space and time, and $M_n^k$ is the model output for component k. $C_k$ is the covariance matrix. Equation (12) incorporates the assumption that the difference between data and model, i.e., the error of the model approximation is normally distributed. Based on the Gaussian approximation on the error, Equation (11) can be simplified. It concerns the derivative of a quadratic form, which is evaluated using the corresponding matrix identity [4]. Substituting the derivative of the quadratic form produces:

$$\sum_T\sum_N P(k\mid n)C_k^{-1}(X_n-M_n^k)\frac{\partial M_n^k}{\partial \Theta_{k,i}} = 0 \quad (13)$$

The derivative of the model with respect to the parameters is evaluated using the given form of the model for the EEG identification task, as discussed in the next section. Note that $C_k^{-1}$ is constant and can be omitted from the above equation.

The Case when $r_k(t)$ Depends on $\theta_{k,i}$

This case is governed by the following extended equation, which now includes the terms corresponding to the partial derivatives of $r_k(t)$:

$$-\sum_T\sum_N P(k\mid n)\left\{\frac{\partial \ln(p(X_n\mid \Theta_{k,i}))}{\partial \Theta_{k,i}} + \frac{\partial \ln(r_k(t))}{\partial \Theta_{k,i}}\right\} - \lambda\sum_T \frac{\partial r_k(t)}{\partial \Theta_{k,i}} = 0 \quad (14)$$

Again, the Gaussian assumption on the error term as given by Equation (12) is used. By performing the derivation of the quadratic form, the following condition is derived:

$$\sum_T\sum_N P(k\mid n)\left\{C_k^{-1}(X_n-M_n^k)\frac{\partial M_n^k}{\partial \Theta_{k,i}} + \frac{\partial \ln(r_k(t))}{\partial \Theta_{k,i}}\right\} = \lambda\sum_T \frac{\partial r_k(t)}{\partial \Theta_{k,i}} \quad (15)$$

Equation (15) is a generalization of Equation (13). If $r_k(t)$ does not explicitly depend on the model parameters, then the corresponding derivatives are zero, and the above equation reduces to Equation (13). To evaluate these equations, the functional form of the EEG model should be specified. This is provided in the next section.

Implementation of Dynamic Logic for Phase Cones

Geometry of the Cones

Consider the time evolution of a process evolving over a 2-dimensional array $h(\xi,\eta,t)$. Variables $\xi$ and $\eta$ denote the two orthogonal coordinates in the Euclidean plane, and t is the time variable. The two spatial coordinates vary over an M×M square array, which is the spatial window demarcated by the EEG array placed over the cortical surface. The observation is conducted over the time interval (0, T). Quantity $h(\xi,\eta,t)$ denotes the analytic phase at the given space and time instant. (The experiments discussed herein consider a simulated EEG data set.) Physiological evidence shows that phase cones may exist for some time duration in EEG data [2], which is model in the simulations as follows.

For some time, there may not be any phase cone over the array. In that case, the data reflect random oscillations over space and time. At a certain time instant $t_A$, a cone may start growing at point $(\xi_A,\eta_A)$, which is called the apex of the cone. The cone is characterized by growth velocity $v_r$ in radial direction, and by temporal gradient of growth $v_b$. For example, at time $\tau$ after the incipience, $\tau = t - t_A \geq 0$, the cone extends to a circular area marked by the phase front of radius $\tau = v_r \times \tau$ around the starting point $(\xi_A,\eta_A)$. The cones exist for time duration $\tau_{max}$ and they dissolve afterwards.

The height of the cone at any instant is determined by $v_b$ and by the distance from the apex. At the exact location of the apex $(\xi_A,\eta_A)$, the phase linearly increases with time during the existence of the cone:

$$h(\xi_A,\eta_A,t) = v_b(t-t_A) \quad t_A \leq t \leq t_A + \tau_{max} \quad (16)$$

The Euclidean distance d of point $(\xi,\eta)$ from the apex is given as $d = \sqrt{(\xi-\xi_A)^2 + (\eta-\eta_A)^2}$. The value of h is given by the height of the cone at the given space and time point. (See FIG. 1).

$$h(\xi, \eta, t) = v_b t - \frac{v_b}{v_r}\sqrt{(\xi - \xi_A)^2 + (\eta - \eta_A)^2} \qquad (17)$$

for time values: $t_A \leq t \leq t_A + \tau_{max}$ and zero outside of this time interval. The above equation is used for spatial locations inside the cone front, with h=0 outside.

Figure 2:
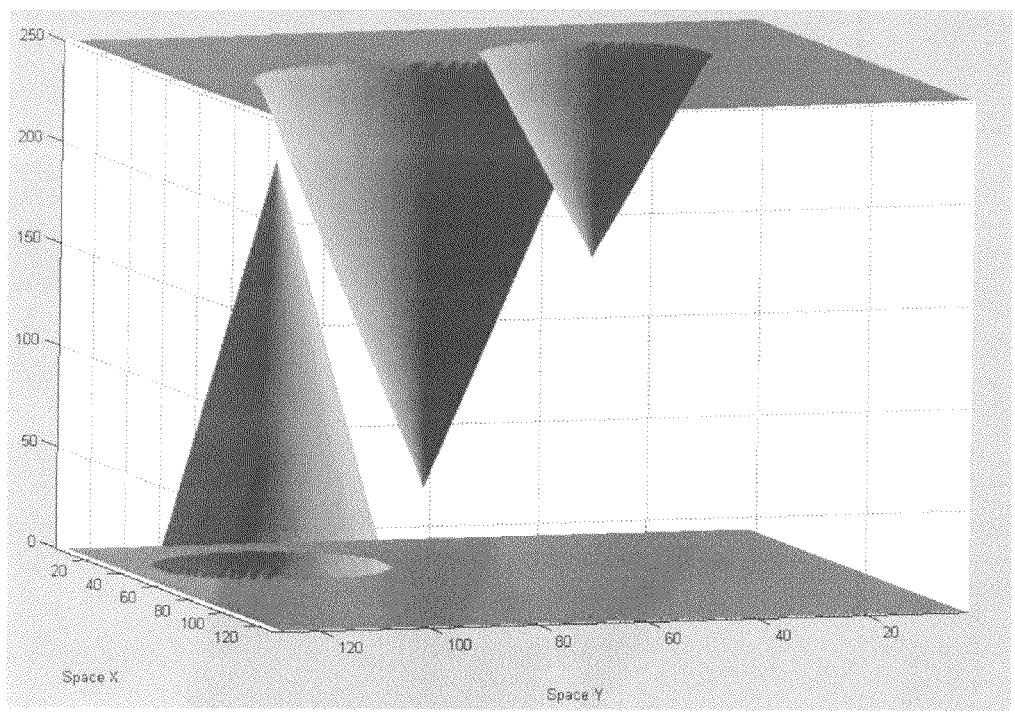
FIG. 2 is an illustration of simulations with multiple phase cones and no noise.

Example of results of simulation with multiple phase cones evolving over time is show in FIG. 2. Note that cones may overlap in time and space. This model assumes fixed values of radial velocity $v_r$ and temporal gradient $v_b$, as indicated by cortical experiments. FIG. 2 shows positive and negative phase cones, as observed in EEG. A negative cone results in a negative sign of the time gradient $v_b$.

DL Equations for Phase Cone Parameters

In order to derive the explicit equations for phase cone identification, the model description as defined by Equation (17) is inserted into Equations (13) and (15). It is necessary to specify the form of the weight coefficient $r_k(t)$. $r_k(t)$ is defined as the proportion of the space-time volume occupied by the k-th cone at time t. This is calculated as the ratio of the volume of the phase cone and the total observed space-time volume, given below:

$$r_k(t) = \frac{v_r^2 v_b \pi (t - t_A)^3}{3V_o}, \text{ if } 0 \leq t - t_A \leq \tau_{max} \qquad (18)$$

Here $V_o$=M×M×T is the volume of the observed space-time region, which is a 2-dimensional square area of side M extending in time for duration T. It is assumed that the k-th cone is given by the initiation points ($\xi_A, \eta_A, t_A$). Note, that it is assumed that coefficients $v_r$ and $v_b$ are not estimated in this study, rather their values are fixed and determined based on the properties of the cortical tissue. For brevity, the notation $D=v_r^2 v_b \pi/3V_o \cdot r_k(t)$ is a function of initiation parameter $t_A$, but it does not depend explicitly on the spatial apex points. It should be pointed out that such assumption is valid as long as the cones are completely inside the observed volume. If the size of the observed volume is much larger than the cone, this assumption is reasonable. However, for large cones extending beyond the observation volume, this simplification is less accurate. The present study does not consider the effect of cones extending beyond the observation space.

Estimation of Spatial Apex Coordinates

Start with Equation (13) and substitute the expression for the derivative of the k-th model with respect to apex points $\xi_A$ and $\eta_A$. The discussions below consider the case of $\xi_A$, while equations for $\eta_A$ can be derived in a similar way. The model equation is rewritten as:

$$M_x^k = v_b(t - t_A) - \frac{v_b}{v_r}\sqrt{(\xi - \xi_A)^2 + (\eta - \eta_A)^2} \qquad (19)$$

Standard algebra produces the following equation.

$$\sum_T \sum_N P(k|n) C_k^{-1} (X_n - M_n^k) \frac{v_b}{v_r} \frac{(\xi - \xi_A)}{\sqrt{(\xi - \xi_A)^2 + (\eta - \eta_A)^2}} = 0 \qquad (20)$$

This leads to an expression for unknown parameter $\xi_A$:

$$\xi_A = \frac{\langle (X_n - M_n^k)\xi \rangle_{k,c}}{\langle (X_n - M_n^k) \rangle_{k,c}} \qquad (21)$$

A similar equation is valid for model parameter $\eta_A$:

$$\eta_A = \frac{\langle (X_n - M_n^k)\eta \rangle_{k,c}}{\langle (X_n - M_n^k) \rangle_{k,c}} \qquad (22)$$

Here the generalized bracket notation is introduced which includes a cylindrical kernel for the k-th model component:

$$\langle * \rangle_{k,c} = \sum_T \sum_N P(k|n) \frac{*}{\sqrt{(\xi - \xi_A)^2 + (\eta - \eta_A)^2}} \qquad (23)$$

Using Equations (21) and (22), unknown parameters $\xi_A$ and $\eta_A$ can be estimated. It is clear that the model is a function of these parameters, so the parameters can not be determined. Instead, an iterative learning procedure is used as described in the next section.

Estimation of the Time of Initiation of the Cone:

Start with Equation (15) and substitute the expression of the derivative of the k-th model and $r_k(t)$ with respect to initiation time $t_A$. This equation is more complicated as the spatial apex case addressed previously. Using Equation (18) produces the following expressions for the derivatives:

$$\frac{\partial M_n^k}{\partial t_A} = -v_b; \frac{\partial \ln r_k(t)}{\partial t_A} = \frac{-3}{t - t_A}; -\sum \frac{\partial r_k(t)}{\partial t_A} = D\tau_{max}^3 \qquad (24)$$

D is a constant, which is a shorthand introduced following Equation (18). Substituting these derivatives into Equation (15) produces:

$$\left\langle \frac{1}{t - t_A} \right\rangle_k = \frac{v_B C_k^{-1}}{3} \langle (x_n - M_n^k) \rangle_k + \frac{\lambda}{3} D\tau_{max}^3 \qquad (25)$$

This is a transcendental equation and it is to be solved numerically. The right hand side of the equation is constant, and by changing $t_A$, an approximate solution can be found. Note that the bracket notation now does not include the cylindrical kernel:

$$\langle * \rangle_k = \Sigma \Sigma P(k|n) * \qquad (26)$$

Iterative Algorithm for Phase Cone Identification

Figure 3:
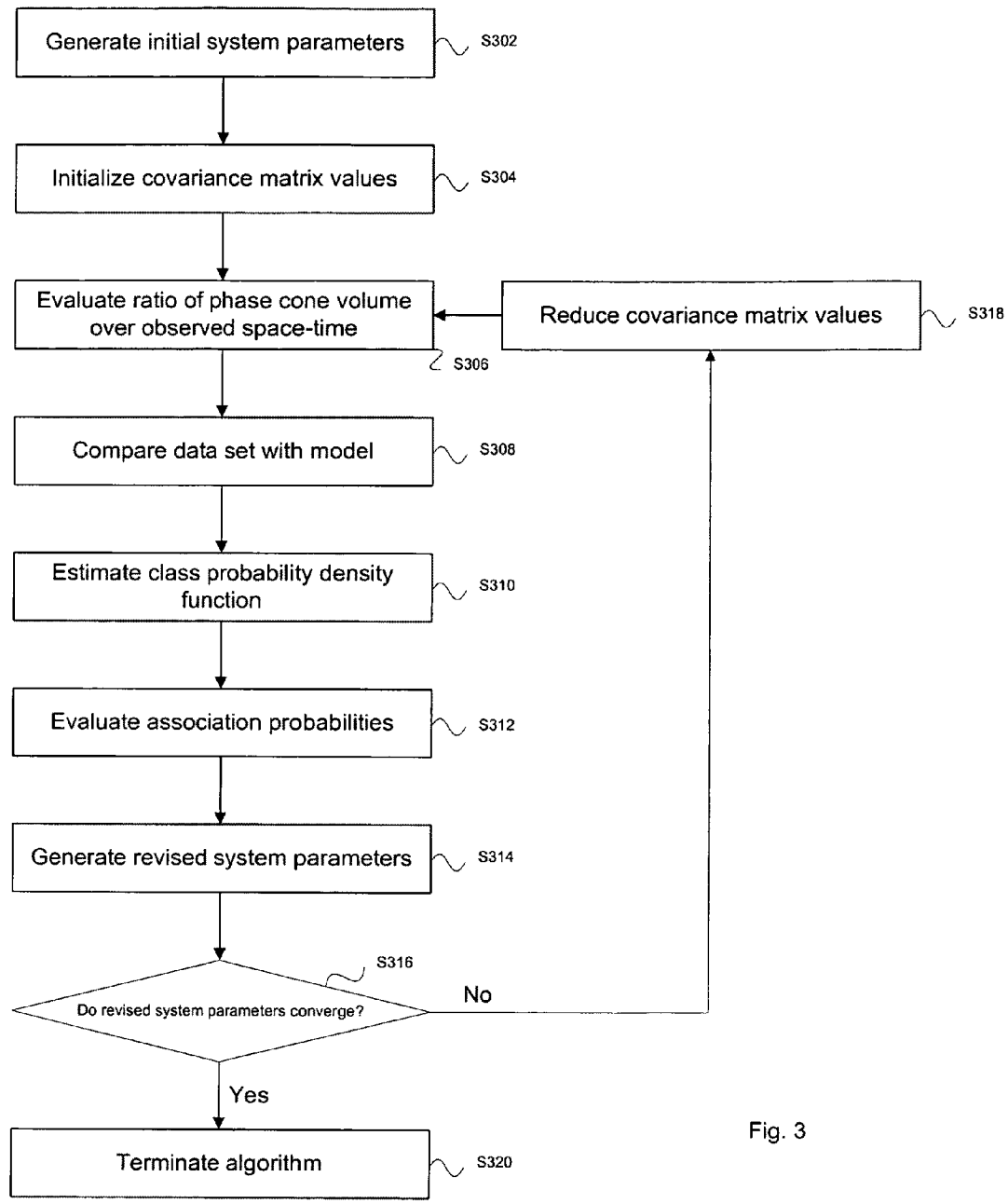
FIG. 3 is a flow chart of a method for identifying phase cone identification according to one embodiment of the invention.

Based on the above equations, an algorithm is outlined for the iterative solution of the DL equations for the phase cone problem. This has the following steps as depicted in FIG. 3:

1) Initialize the system with a starting estimation of parameters ($\xi_A, \eta_A, t_A$) for a preset number of cone components (S302). Also, initialize the covariances $C_k$ at a suitable high value, as indicated in Equation (18) (S304).

2) Evaluate $r_k(t)$ using the obtained initiation parameter $t_A$ (S306).

3) Evaluate the model with these parameters (S308) and obtain estimation of class probability density functions $p(X_n|\Theta_k)$ (S310), using Equation (12).

4) Evaluate association probabilities p(k|n) using Equation (8) (S312).

5) Using Equations. (21), (22), and (25), calculate a revised set of parameters (S314). The revised set of parameters are compared with previous parameter sets for convergence (S316). The algorithm iterates until parameters converge (S318).

Experience indicates that this iteration converges relatively quickly, in about 100 iterations or less. During the process, the covariance values is continuously decreased to approach the desired base level (S316).

The inventions described herein provide a Dynamic Logic-based algorithm for the detection of spatio-temporal transient processes in brains. The derived mathematical formalism can be used for the estimation of the parameters of propagating phase cones. The inventions also provide an algorithm for the iterative solution of these equations.

Although the inventions herein are described in the context of identifying phase gradients in EEG signals, one of skill in the art will readily recognize the applicability of the inventions described herein to other data analysis applications.

Likewise, one skilled in the art will readily recognize that the method described herein can be implemented on computer readable media or a system. An exemplary system includes a general purpose computer configured to execute the methods described herein. Such a system can be connected directly or through a network to an EEG monitor for real-time or delayed analysis of a subject's brain activity.

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, clients, servers and the like) shown as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

INCORPORATION BY REFERENCE

The entire contents of all patents, published patent applications, and other references cited herein are hereby expressly incorporated herein in their entireties by reference.

REFERENCES

[1] Freeman W. J., Burke B. C., Holmes M. D. (2003) Aperiodic phase re-setting in scalp EEG of beta-gamma oscillations by state transitions at alpha-theta rates. Hum. Brain Mapping, 19: 248-272.

[2] Freeman W. J. (2004) Origin, structure, and role of background EEG activity. Part 2. Analytic phase. Clin. Neurophysiol. 115: 2089-2107.

[3] Skarda, C. A., W. J. Freeman (1987) How brains make chaos in order to make sense of the world, Behav. Brain Sci., 10, 161-195.

[4] Freeman, W. J. (1991) The physiology of perception, Scientific American, 264(2), 78-85.

[5] Freeman, W. J., Kozma, R. (2000) Local-global interactions and the role of mesoscopic (intermediate-range) elements in brain dynamics. Behavioral and Brain Sciences, 23, 401.

[6] Barrie J M. Freeman W J, Lenhart M. (1996) Modulation by discriminative training of spatial patterns of gamma EEG amplitude and phase in neocortex of rabbits. J. Neurophysiol. 76: 520-539.

[7] Perlovsky, L. I. (2001) "Neural Networks and Intellect Using Model Based Approach," Oxford University Press, Oxford, U.K.

[8] Perlovsky, L. I. (2006) Toward physics of the mind: Concepts, emotions, consciousness, and symbols. Physics of Life Reviews, 3(1), 23-55.

[9] Deming, R. (1998) Reconstruction of Time-varying Objects in Computerized Tomography using a Model-based Neural Network, Proc. STIS98: Joint Conf. Sci. and Technol. Intell. Systems, ISIC/CIRA/ISAS, Gaithersburg, Md., September 14-17, pp. 422-427.

[10] Deming, R. (2005) Parameter Estimation for Mixtures. Internal Report, Aug. 22, 2005.

[11] Deming, R., Perlovsky, L. I. (2006). Robust detection and spectrum estimation of multiple sources from rotating-prism spectrometer images. Proc. SPIE, 6365.

[12] Linnehan, R., J. Schindler, D. Brady, R. Kozma, R. Deming, L. Perlovsky (2007) Dynamic Logic Applied to SAR data for parameter Estimation Behind Walls, IEEE Radar Conference, Waltham, Mass., April 2007.

[13] Perlovsky, L. I. Schoendorf, W. H. Burdick, B. J. Tye, D. M. (1997) Model-based neural network for target detection in SAR images. IEEE Transactions on Image Processing, 6(1), 203-216.

[14] Perlovsky, L., R. Deming (2005) A Mathematical Theory for Learning, and Its Application for Time varying Computer Tomography, New Mathematics and Natural Computation, 1(1), pp. 147-171.

[15] Kozma, R., Freeman, W. J. (2002) Classification of EEG Patterns Using Nonlinear Neurodynamics and Chaos, Neurocomputing, 44-46, 1107-1112.

[16] Kozma, R., R. Deming, L. Perlovsky (2007) Estimation of Propagating Phase Transients in EEG Data—Application of Dynamic Logic Neural Modeling Approach, Proc. International Joint Conference on Neural Networks, IJCNN'07, pp. 1602-1606.

[17] Duda, R. O., and Hart, P. E. (1973) "Pattern Classification," Wiley and Sons, New York.

The invention claimed is:

1. A computer-implemented method for identifying phase cones in a data set, the method comprising:
    (a) generating an initial set of values of parameters ($\xi_A, \eta_A, t_A$) for a preset number of cones on a computer;
    (b) initializing a covariance matrix with high values on the computer;
    (c) evaluating the ratio of volume of a phase cone over total observed space-time volume on the computer;
    (d) comparing the data set with a model on the computer;
    (e) estimating a class probability density function on the computer;
    (f) evaluating association probabilities on the computer; and
    (g) generating a revised set of values of parameters ($\xi_A, \eta_A, t_A$) on the computer.

2. The method of claim 1, further comprising:
    repeating steps (c) through (g) with the revised set of values.

3. The method of claim 2, further comprising:
reducing the values of the covariance matrix.

4. The method of claim 2, wherein the repeating step is terminated when the revised set of values of parameters ($\xi_A$, $\eta_A$, $t_A$) converge.

5. The method of claim 1, wherein the ratio of the volume of the phase cone over the total observed space-time volume is expressed by $$r_k(t) = \frac{v_r^2 v_b \pi (t - t_A)^3}{3 V_o}.$$

6. The method of claim 1, wherein $\xi_A$ in the revised set of values of parameters ($\xi_A, \eta_A, t_A$) is defined by the expression $$\xi_A = \frac{\langle (X_n - M_n^k) \xi \rangle_{k,c}}{\langle (X_n - M_n^k) \rangle_{k,c}}.$$

7. The method of claim 1, wherein $\eta_A$ in the revised set of values of parameters ($\xi_A, \eta_A, t_A$) is defined by the expression $$\eta_A = \frac{\langle (X_n - M_n^k) \eta \rangle_{k,c}}{\langle (X_n - M_n^k) \rangle_{k,c}}.$$

8. The method of claim 1, wherein $t_A$ in the revised set of values of parameters ($\xi_A, \eta_A, t_A$) is defined by the expression $$\left\langle \frac{1}{t - t_A} \right\rangle_k = \frac{v_B C_k^{-1}}{3} \langle (x_n - M_n^k) \rangle_k - \lambda D r_{max}^3.$$

9. The method of claim 1, wherein the model is represented by the expression $$h(\xi, \eta t) = v_b t - \frac{v_b}{v_r} \sqrt{(\xi - \xi_A)^2 + (\eta - \eta_A)^2}.$$

10. The method of claim 1, wherein the class probability density function is represented by the expression $$p(X_n \mid \Theta_k) = \frac{1}{\sqrt{(2\pi)^3 |C_k|}} e^{\left\{ -\frac{1}{2} |X_n - M_n^k|^T C_k^{-1} |X_n - M_n^k| \right\}}.$$

11. The method of claim 1, wherein the association probabilities are represented by the expression $$P(k \mid n) = \frac{r_k(t) p(X_n \mid \Theta_k)}{\sum_K r_k(t) p(X_n \mid \Theta_k)}.$$

12. A computer-readable medium whose contents cause a computer to perform a method for identifying phase cones in a data set, the method comprising:
(a) generating an initial set of values of parameters ($\xi_A, \eta_A, t_A$) for a preset number of cones;
(b) initializing a covariance matrix with high values;
(c) evaluating the ratio of volume of a phase cone over total observed space-time volume;
(d) comparing the data set with a model;
(e) estimating a class probability density function;
(f) evaluating association probabilities; and
(g) generating a revised set of values of parameters ($\xi_A, \eta_A, t_A$).

13. A system comprising:
a computer-readable medium as recited in claim 12; and
a computer in data communication with the computer-readable medium.

14. The method of claim 1, wherein the data set is an electroencephalography data set.

* * * * *